(12) United States Patent
Zamore

(10) Patent No.: US 6,596,818 B1
(45) Date of Patent: *Jul. 22, 2003

(54) IRRADIATION CONVERSION OF THERMOPLASTIC TO THERMOSET POLYMERS

(76) Inventor: Alan M. Zamore, 23 Mountain Ave., Monsey, NY (US) 10952

( * ) Notice: Subject to any disclaimer, the term of this patent is extended or adjusted under 35 U.S.C. 154(b) by 0 days.

This patent is subject to a terminal disclaimer.

(21) Appl. No.: 08/947,000

(22) Filed: Oct. 8, 1997

Related U.S. Application Data

(63) Continuation-in-part of application No. 08/727,145, filed on Oct. 8, 1996, now Pat. No. 5,900,444.

(51) Int. Cl.$^7$ ............... C08J 3/28; C08J 3/24; C08F 283/02; C08F 283/04; C08F 283/06; A61L 29/06; A61M 25/10; A61M 25/00

(52) U.S. Cl. ............... 525/426; 2/159; 2/161.7; 36/25 R; 36/32 R; 128/844; 399/350; 522/134; 522/135; 522/136; 522/137; 522/138; 522/141; 522/142; 522/143; 522/144; 522/162; 522/164; 522/165; 522/166; 525/445; 525/529; 525/530; 604/96.01; 604/103.11; 604/264; 604/349; 604/523; 604/532; 604/915; 606/7; 606/228; 606/231

(58) Field of Search ............... 2/159, 161.7, 167, 2/168; 128/844; 156/272.2, 275.5, 275.7; 427/487, 488, 491, 496, 501, 505, 506, 507, 508, 513, 516, 520; 428/411.1, 423.1, 425.1, 425.6, 425.8, 431, 435, 441, 458, 461, 474.4, 477.7, 479.3, 479.6, 480, 481, 482, 500, 511, 523; 522/90, 96, 113, 114, 116, 139, 140, 160, 168, 173, 176, 178, 179, 181, 188; 525/50, 123, 127, 128, 165, 175, 176, 178, 181, 182, 183, 193, 241, 279, 281, 282, 304, 306, 311, 313, 333.3, 333.6, 374, 375, 383, 386, 417, 455, 539, 540; 528/75, 288, 289, 326, 327, 345, 363, 392, 405, 417, 421, 423, 425

(56) References Cited

U.S. PATENT DOCUMENTS

| | | | | |
|---|---|---|---|---|
| 3,658,670 A | | 4/1972 | Holicky et al. ............. 522/106 |
| 3,719,539 A | * | 3/1973 | Lamb et al. ............... 264/236 |
| 4,013,806 A | * | 3/1977 | Volkert et al. ............... 427/54 |
| 4,025,407 A | | 5/1977 | Chang et al. ............... 522/142 |
| 4,065,589 A | * | 12/1977 | Lenard et al. ............... 428/35 |
| 4,101,699 A | * | 7/1978 | Stine et al. ............... 428/36 |
| 4,133,731 A | | 1/1979 | Hansen et al. ............. 428/508 |
| 4,151,057 A | | 4/1979 | St. Clair et al. ............ 428/508 |
| 4,264,658 A | | 4/1981 | Tobias et al. ............... 428/35 |
| 4,266,005 A | * | 5/1981 | Nakamura et al. .......... 430/271 |
| 4,358,354 A | * | 11/1982 | Iida et al. ............... 204/159.15 |
| 4,444,816 A | | 4/1984 | Richards et al. ............. 428/36 |
| 4,654,233 A | * | 3/1987 | Grant et al. ............... 427/379 |
| 4,687,689 A | * | 8/1987 | Yazaki et al. ............... 428/35 |
| 4,762,884 A | * | 8/1988 | Goyert ............... 525/28 |
| 4,820,782 A | * | 4/1989 | Ueno ............... 525/454 |
| 4,871,811 A | * | 10/1989 | Gaku et al. ............... 525/148 |
| 5,236,978 A | * | 8/1993 | Selvig et al. ............... 524/81 |
| 5,284,883 A | * | 2/1994 | Ueno et al. ............... 522/79 |
| 5,334,201 A | * | 8/1994 | Cowan ............... 623/1 |
| 5,336,585 A | * | 8/1994 | Takahashi et al. .......... 430/284 |
| 5,438,106 A | * | 8/1995 | Siranovich et al. ......... 525/440 |
| 5,442,036 A | | 8/1995 | Beavers et al. ............. 528/296 |
| 5,455,308 A | * | 10/1995 | Bastiaansen ............... 525/407 |
| 5,576,072 A | * | 11/1996 | Hostettler et al. .......... 427/532 |
| 5,733,496 A | | 3/1998 | Avellant ............... 264/470 |
| 5,779,729 A | | 7/1998 | Severini ............... 606/191 |
| 5,993,415 A | | 11/1999 | O'Neil et al. ............... 604/96 |
| 5,998,551 A | | 12/1999 | O'Neil et al. ............... 525/426 |

FOREIGN PATENT DOCUMENTS

| | | |
|---|---|---|
| EP | 0-214-602 | 2/1986 |
| JP | 61174256 | 5/1986 |
| WO | WO 82/0204 | 6/1982 |
| WO | WO 95/23619 | 9/1995 |
| WO | WO 98/55171 | 12/1998 |
| WO | WO 0119425 | 3/2001 |

\* cited by examiner

*Primary Examiner*—Rabon Sergent
(74) *Attorney, Agent, or Firm*—Dale L. Carlson; Wiggin & Dana LLP

(57) ABSTRACT

Disclosed is a radiation-crosslinkable thermoplastic polymer composition, a process for the preparation thereof, an angioplasty balloon made using such a composition, and a method of using the angioplasty balloon. The composition contains a reactive monomer cross-linker, that facilitates cross-linking of the reaction product upon contact of the cross-linker-containing composition with a particle beam from a radiation source.

36 Claims, No Drawings

IRRADIATION CONVERSION OF THERMOPLASTIC TO THERMOSET POLYMERS

CROSS REFERENCE TO RELATED APPLICATION

This application is a Continuation-In-Part of U.S. application Ser. No. 08/727,145, filed on Oct. 8, 1996 now U.S. Pat. No. 5,900,444.

FIELD OF THE INVENTION

This invention relates generally to the conversion of thermoplastic polymers into thermoset polymers and more specifically to such thermoset polymers exhibiting improved physical and chemical properties, relative to the corresponding thermoplastic polymers. Illustrative of such polymers are thermoset polyurethanes which are advantageously prepared using aliphatic diisocyanates and a reactive monomer crosslinker.

BACKGROUND OF THE INVENTION

Thermoplastic polymers, such as thermoplastic polyurethanes, are relatively easy to process into a wide variety of fabricated products. Unfortunately, however, the high temperature stability of these polymers and their physical properties such as mechanical strength at elevated temperatures, as well as their stability in some commonly-used organic solvents, are less than might be desired. Accordingly, methodology has been developed to provide heat-induced crosslinking to convert thermoplastic polymers, such as thermoplastic polyurethanes, into thermoset polyurethanes having the desired stability at high temperatures and in the presence of solvents. By way of illustration, U.S. Pat. No. 4,255,552 discloses thermoset polyurethane elastomers obtained by adding organic peroxides to a liquid polyurethane-forming composition prior to reacting the composition to form the polyurethane. The '552 patent teaches that the liquid polyurethane-forming composition containing "unactivated hydrogen peroxide" may be formed into a desired article and then heated to thermoset the article, or provided in solid form such as sheet, crumbs, or granules which are then formed into a desired article that is then thermoset by heating the article. The organic peroxides disclosed in the '552 patent are said to have a half-life of greater than one hour at 100° C. Unfortunately, these peroxide-containing compositions are less stable than might be desired during melt processing or thermoforming of the polyurethane composition into the desired finished article, thus providing technology that is not commercially practical.

As an alternative to heat induced crosslinking of thermoplastic polyurethanes, their conversion into thermoset polyurethanes by irradiation is known in the art. A technical journal article entitled "Radiation Crosslinked Thermoplastic Polyurethane", published in the journal *International Polymer Science and Technology*, Vol. 19, No. 1, pp. T/6–T/9 (1992), discloses the production of such thermoset polyurethanes using a polyisocyanate and methacrylate monomer as a radiation-cross-linkable monomer. This technical journal article does not disclose the particular polyisocyanate used in making polyurethanes disclosed therein. Unfortunately, methacrylate is more heat sensitive than otherwise might be desired, causing a risk of premature cross-linking during storage, shipping, or processing, and prior to the desired conversion of the thermoplastic polyurethane into a thermoset polyurethane. Further, not all polyisocyanates perform alike in irradiation-crosslinking of TPUs. Indeed, the present inventor has been unsuccessful in attempts to cross-link TPU formulations based upon aromatic polyisocyanates to provide a desirable article.

Instead of cross-linking, the resulting article exhibits an undesirable discoloration.

U.S. Pat. No. 4,762,884 issued Aug. 9, 1988 for "Process for the Production of Radiation-Crosslinked Thermoplastic Polyurethanes". This patent discloses the use of a cross-linking agent being a monomeric acrylate or methacrylates. These acrylates and methacrylates are more heat sensitive than might otherwise be desired. Further, although this patent discloses polyisocyanates generally, with a preference for aromatics, the present inventor (as pointed out hereinabove) has been unsuccessful in attempts to cross-link TPU formulations based upon aromatic polyisocyanates to provide a desirable article. As stated above, instead of cross-linking, the resulting article exhibits an undesirable discoloration.

Irradiation-induced cross-linking of other polymers, such as nylon, is known in the prior art, the use of these other polymers for property enhancement, such as the conversion of the nylon from a thermoplastic to a thermoset polymer in the form of an angioplasty balloon within the blood vessels of a human or other mammal, has not been disclosed heretofore to the knowledge of the present inventor.

In view of the above, there is a continuing need in the polymers manufacturing community for new polymer compositions that are readily thermoset by cross-linking when desired, but also less sensitive to unwanted heat-induced cross-linking during storage and prior to use than prior art compositions, such as the above-discussed prior art polyurethane-forming compositions, most notably prior art peroxide, acrylate, and methacrylate-containing compositions. Such compositions desirably would provide advantageous processing capability, such as by extrusion, when the composition is in the thermoplastic state, and advantageous elevated temperature stability and solvent resistance when the composition is thermoset after formation into the desired product. Moreover, new uses for compositions known to be cross-linkable in the presence of irradiation, such as nylon, would also be desirable. The present invention provides such desirable polymer compositions, together with processes for the production of the composition, as well as new uses for compositions known to be irradiation cross-linkable, such as nylon.

SUMMARY OF THE INVENTION

In one aspect, the present invention relates to a radiation-crosslinkable polymer composition comprising:

(a) a polymer selected from the group consisting of polyurethanes, styrene-based polymers, polyester-based polymers, polyether-based polymers, polyamide-based polymers, polylaurinlactam-based polymers, polytetrahydrofuran-based polymers, and combinations thereof, and (b) a reactive monomer for cross-linking at least a portion of said polymer upon contacting said reactive monomer energy, such as ionizing radiation particles, from a radiation source. The "polymer" referred to in component (a) is intended to encompass polymers comprising the recited base component, as well as co-polymers containing the recited base component polymerized with a separate monomeric component. Preferably, the polymer of component (a) comprises a block co-polymer containing hard and soft segments. The "ionizing radiation particles" referred to in component (b) is intended to encompass any such particles, including photons, beta-particles and gamma-particles, or a combination thereof, emitted from a radiation source. Illustrative sources for such "ionizing radiation particles" include electron-beam radiation, ultraviolet radiation, and combinations thereof.

In another aspect, the present invention relates to a radiation-crosslinkable thermoplastic polyurethane composition comprising:
(a) a polyurethane produced by reacting:
  (i) an aliphatic polyisocyanate, and
  (ii) a polyahl, and
(b) a reactive monomer for cross-linking at least a portion of said polyurethane upon contacting said reactive monomer with ionizing radiation particles from a radiation source.

In still another aspect, the present invention relates to a process for preparing a thermoplastic article and for converting the thermoplastic article to a thermoset article, said process comprising the steps of:
(a) preparing a thermoplastic polymer product by mixing a solid, extrudable thermoplastic polymer product with a solid or liquid reactive monomer cross-linker and a polymer selected from the group consisting of nylon, polyurethanes, styrene-based polymers, polyester-based polymers, polyether-based polymers, polyamide-based polymers, polyaurinlactam-based polymers, polytetrahydrofuran-based polymers, and combinations thereof, (advantageously, in one embodiment causing said solid thermoplastic polymer product to adsorb or absorb liquid reactive monomer, thus providing a solid thermoplastic admixture),
(b) forming said thermoplastic mixture into a desired thermoplastic article, and .
(c) irradiating said article with a particle beam in order to cause said reactive monomer cross-linker in said product to cross-link at least a portion of said polymer, thereby converting said article into a thermoset article, said thermoset article exhibiting enhanced properties, such as enhanced melt stability, relative to said thermoplastic article.

In still another aspect, the present invention relates to a process for converting a thermoplastic polyurethane to a thermoset polyurethane. The process comprises the steps of:
(a) preparing a liquid or solid thermoplastic polyurethane composition comprising a reactive monomer cross-linker and a reaction product of:
  (i) an aliphatic polyisocyanate, and
  (ii) a polyahl, and
(b) irradiating said composition with a particle beam (preferably a beam of photons) in order to cause said reactive monomer cross-linker in said composition to cross-link at least a portion of said reaction product, thereby converting said composition into said thermoset polyurethane.

In yet another aspect, the present invention relates to a process for preparing a thermoplastic polyurethane and converting the thermoplastic polyurethane to a thermoset polyurethane comprising the steps of:
(a) preparing a liquid or solid thermoplastic polyurethane-forming composition comprising a reactive monomer cross-linker and also comprising:
  (i) an aliphatic polyisocyanate, and
  (ii) a polyahl, and
(b) reacting said aliphatic polyisocyanate with said polyahl to form a polyurethane composition containing said cross-linker, and (c) irradiating said polyurethane composition with a beam of photons in order to cause said reactive monomer cross-linker in said composition to cross-link at least a portion of said reaction product, thereby converting said composition into said thermoset polyurethane.

In yet another aspect, the present invention relates to a process for producing a thermoset product which comprises irradiating a thermoplastic elastomer composition containing a reactive monomer cross-linker in order to cross-link said thermoplastic elastomer to convert the thermoplastic elastomer to said thermoset product, said thermoplastic elastomer composition comprising a component selected from the group consisting of styrenic co-polymers, co-polyester polymers, co-polyamide polymers, a reaction product of polyaurinlactam and polytetrahydrofuran, a reaction product of an aliphatic polyisocyanate and a polyahl; and, combinations thereof.

In yet another aspect, the present invention relates to a cross-linkable angioplasty balloon suitable for irradiation-induced cross-linking, said angioplasty balloon comprising a radiation-crosslinkable polymer composition comprising (a) a component selected from the group consisting of nylon, styrenic co-polymers, co-polyester polymers, co-polyamide polymers, a reaction product of polylaurinlactam and polytetrahydrofuran, a reaction product of an aliphatic polyisocyanate and a polyahl; and, combinations thereof, and (b) a reactive monomer cross-linker in an amount sufficient to provide cross-linking of at least a portion of said polymer or copolymer upon contacting said cross-linker with ionizing photons from a radiation source.

In yet another aspect, the present invention relates to a method of using an angioplasty balloon that is produced from a thermoplastic polymer converted to a thermoset polymer, wherein the balloon comprises the reaction product of a radiation-crosslinkable polymer composition comprising (a) a component selected from the group consisting of nylon, poly(1,4-butanediol terephthalate), styrenic co-polymers, co-polyester polymers, co-polyamide polymers, a reaction product of polyaurinlactam and polytetrahydrofuran, a reaction product of an aliphatic polyisocyanate and a polyahl; and, combinations thereof, and (b) a reactive monomer cross-linker in an amount sufficient to provide cross-linking of at least a portion of said polymer or copolymer upon contacting said cross-linker with radiation (such as free radical-initiating or ionizing photons) from a radiation source, said method comprising the steps of:
(i) forming a tube from said radiation-crosslinkable polymer composition,
(ii) irradiating said tube with a beam of particles in order to cause said radiation-crosslinkable polymer composition to crosslink, thereby converting said tube from a thermoplastic to a thermoset state, said thermoset state exhibiting enhanced properties relative to said thermoplastic state,
(iii) heat expanding a portion of the tube to provide a balloon in said tube, and deflating said balloon,
(iv) inserting said tube containing said balloon, in a deflated state, into a desired blood vessel within a human or other mammal body, and moving said balloon to a desired site within said blood vessel, and
(v) inflating said balloon to an inflated state at said desired site to provide an inflated balloon.

In another aspect, the present invention relates to a process for fabricating a tube containing an angioplasty balloon from a crosslinkable polymer composition comprising (a) a component selected from the group consisting of nylon, poly(1,4-butanediol terephthalate), styrenic co-polymers, co-polyester polymers, co-polyamide polymers, a reaction product of polyaurinlactam and polytetrahydrofuran, a reaction product of an aliphatic polyisocyanate and a polyahl; and, combinations thereof, and (b) a reactive monomer cross-linker in an amount sufficient to provide cross-linking of at least a portion of said polymer or copolymer upon contacting said cross-linker with radiation (such as free radical-initiating or ionizing photons) from a radiation source, said process comprising the steps of:

(i) forming a tube from said radiation-crosslinkable polymer composition, (ii) irradiating said tube with a beam of particles in order to cause said radiation-crosslinkable polymer composition to crosslink, thereby converting said tube from a thermoplastic to a thermoset state, said thermoset state exhibiting enhanced properties relative to said thermoplastic state, (iii) heat expanding a portion of the tube to provide a balloon in said tube, and deflating said balloon, thus forming said tube containing said angioplasty balloon.

In another aspect, the present invention relates to the thermoset polymer products and the thermoset polyurethane products produced by the above-recited processes.

In still another aspect, the present invention relates to a method of forming a coated substrate comprising a substrate and an extrudable solid coating on said substrate, said method comprising applying said coating to said substrate in a thermoplastic state, and converting said coating to thermoset state by free radical initiated crosslinking of the coating in the presence of radiation selected from the group consisting of electron beam radiation, uv radiation, or a combination thereof, to provide a thermoset coating on said substrate characterized by enhanced bonding efficacy to said substrate in said thermoset state relative to said thermoplastic state. The extrudable solid coating is suitably fabricated using a sheet coating, powder coating, or a molded or spray solid coating. Typical substrates include metal, glass, plastic, wood, paper, and combinations thereof. Typical coatings comprise a polymer selected from the group consisting of polyurethanes, styrene-based polymers, polyester-based polymers, polyether-based polymers, polyamide-based polymers, polylaurinlactam-based polymers, polytetrahydrofuran-based polymers, and combinations thereof.

In yet another aspect, the present invention relates to a method of forming a composite comprising two substrates with a coating therebetween, the improvement comprising contacting one side of each of said two substrates with said coating in a thermoplastic state, and converting said coating to a thermoplastic state by free radical initiated crosslinking of the coating in the presence of heat or particle beam radiation selected from the group consisting of electron beam radiation, uv radiation, or a combination thereof, to provide said composite, wherein the thermoset coating in said composite is characterized by enhanced bonding efficacy to said two substrates relative to said thermoplastic state.

A method of forming a composite comprising a substrate and a coating on said substrate, said method comprising applying said coating to said substrate in a thermoplastic state, and converting said coating to a thermoplastic state by free radical initiated crosslinking of the coating in the presence of heat or particle beam radiation selected from the group consisting of electron beam radiation, uv radiation, or a combination thereof.

Also disclosed are the coated substrates and composites produced by the above methods.

These and other aspects will become apparent upon reading the following detailed description of the invention.

DETAILED DESCRIPTION OF THE INVENTION

It has now been surprisingly found, in accordance with the present invention, that a wide variety of polymers and copolymers are suitably irradiated in the presence of specific monomeric radiation sensitizers in order to cause the polymer to crosslink, thereby enhancing the resistance of the polymer against thermal and chemical degradation caused by exposure to heat or corrosive chemicals. Advantageously, co-polymers are employed in the compositions of the present invention, and the preferred co-polymers are so-called "block co-polymers". The block co-polymers contain discrete "hard" and "soft" segments that provide alternating aggregated and amorphous regions in the polymer matrix respectively, by virtue of the specific combination of polymers employed in the co-polymer. Without wishing to be bound by any particular theory, it is believed that advantageous result associated with the use of block co-polymers, in accordance with the present invention, is attributable to the propensity for crosslinking induced by ionization radiation to occur primarily within the amorphous (i.e., the soft segment) matrix. Hence, the presence of the amorphous matrix in alternating regions throughout the polymer will promote the desired crosslinking throughout the polymer.

By way of background, block co-polymer-type thermoplastic elastomers exhibit the advantages of rubber-like elasticity and reversible melt transitions, thereby combining features of thermoplastics and rubbers without requiring vulcanization. These block co-polymer-type thermoplastic elastomers combine the further advantages of high melt temperature, low glass transition temperature, elasticity and thermoplasticity in one polymer. Blocks are formed by segregating each co-polymer into a specific polymer region. With proper sequencing and selection of co-polymer molecular weight, the polymer can exhibit the advantageous properties that characterize each block rather than an amalgamation of the unitized polymer. Block co-polymers are typically non random, and instead their backbone exhibits alternating sequences of hard and soft segments. "Hard" blocks reversibly self aggregate below the polymer melt temperature. Polymer tensile strength accrues from these aggregated regions within the polymer. The aggregation provided by virtue of these aggregated regions is reversible, hence these materials behave like they are thermoplastic polymers. Above the melt temperature, the polymer is a viscous liquid. This allows thermoplastic elastomers to be processed using conventional plastics processing equipment with the added advantage of recyclability of scrap that is produced during fabrication of the desired products. "Soft" blocks tend to accumulate in amorphous matrixes providing for regions of polymer elasticity at temperatures above the glass transition point.

There are distinct advantages associated with the ability to convert thermoplastic polymers, particularly block co-polymers, to thermoset polymers in accordance with the present invention. This ability to convert is particularly important since thermoplastic elastomers, in general, and block copolymers specifically, lack the wide temperature performance range of thermoset rubbers, and their compression set, solvent resistance and deformation resistance at high temperatures are generally not as good as the values for those properties as obtained for thermoset elastomers. Thus, these deficiencies are mitigated, or avoided entirely, by virtue of the ready ability to convert thermoplastic elastomers into thermoset elastomers in accordance with the present invention.

As mentioned above, conversion of the thermoplastic to thermoset polymer is suitably effected using ionizing radiation particles, such as photons, beta-particles and gamma-particles, or a combination thereof, emitted from a radiation source. Illustrative sources for such "ionizing radiation particles" include electron-beam radiation, ultraviolet ("uv") radiation, and combinations thereof. UV curing to provide the thermoset polymer is suitably effected using a photon (free radical) initiator, such as the allylic compounds and/or acrylates described herein.

Illustrative copolymers useful in the present invention include (1) styrenic co-polymers including (a)SBS (styrenic polybutadienic), (b) SIS (styrenic polyisoprenic) and (c) S-EB-S (styrenic polyethylene-butylenic) copolymers; (2) co-polyester polymers including copolymers of poly (1,4 butanediol terephthalate) and poly(alkylene ether terephthalate) trademarked under the HYTRIL mark, and (3) co-polyamide polymers including (a) copoly(ether-ester-amide) polymers trademarked under the PEBAX mark, and (b) PA12 elastomers being copolymers of polylaurinlactam and polytetrahydrofuran trademarked under the VESTAMID mark, and the like.

It has also been surprisingly found, in accordance with the present invention, that these polymers or copolymers, together with a radiation-sentisizing monomer, are suitable for fabricating angioplasty balloons made using thermoset tubing in accordance with the present invention. These balloons exhibit excellent properties, including resistance against breakage when the balloon is expanded in a blood vessel to remove occlusions in the blood vessel. If, for example, the angioplasty balloon comprises S-EB-S (Styrenic polyethylene-butylenic) copolymer, the styrene hard segments of the co-polymer provide structural integrity to the balloon, and the amorphous poly(ethylene-butylene) segments provide flexibility to the balloon, an important characteristic during insertion of the balloon into the desired blood vessel while in a thermoplastic state. This balloon also comprises a reactive monomer, e.g. triallylisocyanurate ("TAIC"), for crosslinking copolymer, such as the S-EB-S copolymer. Irradiation of the precursor tubing for making the balloon activates the reactive monomer and causes the amorphous poly(ethylene-butylene) segments to be preferentially crosslinked to provide enhanced structural integrity to the balloon. The enhanced structural integrity of the balloon makes it resistant to brakeage during use of the balloon to remove blockage in the blood vessels.

As additional illustrations, the present invention is suitably employed to prepare thermoplastic surgical gloves that, once irradiated to thermoset the glove material, provides the gloves with enhanced structural integrity and resistance to breakage during use. Also envisioned are thermoset articles possessing a "memory" such as shrink-fitting surgical gloves that are stretched to an oversize before use, and caused to shrink fit tightly to the hand through the action of body heat or by contacting the gloves with warm water just before use. Likewise, the present invention lends itself to use in male and female birth-control sheathes that can similarly be shrink fit plus will resist breakage during usage, or that can be thinner than those conventionally used while having similar (or greater) structural integrity.

In accordance with the present invention, a preferred thermoplastic polymer, namely thermoplastic polyurethane (so-called "TPU") or polyurea or other polymer or co-polymer is suitably converted to a thermoset polyurethane or polyurea using a polymer-forming or preformed polymer in combination with a select reactive monomer that facilitates crosslinking with the polymer in the presence of irradiation. Illustratively, a polyurethane-forming or a preformed polyurethane (or a polyurea-forming or preformed polyurea) composition comprising an aliphatic diisocyanate and a polyahl, or the reaction product thereof, together with a select reactive monomer (preferably an allylic monomer, more preferably an allylic monomer that is essentially free of peroxide, acrylate and methacrylate moieties) as a crosslinking promoter, are mixed and irradiated to provide the desired thermoset product after forming the product from the extrudable solid thermoplastic polymer raw material. Alternatively, the reactive monomer is suitably contacted with a polymer (or a polymer-forming composition for providing such polymer) selected from the group consisting of styrenic co-polymers, co-polyester polymers, co-polyamide polymers, a copolymer reaction product of polyaurinlactam and polytetrahydrofuran, and combinations thereof, and subsequently irradiated to provide a thermoset polymer before or after being formed into a finished product. Irradiating the composition causes the polymer to convert from a thermoplastic state to a thermoset state without encountering the risk of premature cross-linking that has plagued the above-discussed prior art compositions. The resulting thermoset polymer exhibits advantageous physical and chemical properties. For example, the thermoset polyurethane made in accordance with the present invention can be formulated advantageously to be essentially free of discoloration often associated with prior art thermoset polyurethanes made from TPUs. The term "essentially free of discoloration", as used herein, is intended to mean that the thermoset polyurethane of the present invention advantageously exhibits essentially none (or little) of the undesirable yellow, brown or orange discoloration that typically characterizes thermoset resins produced in accordance with the aforementioned prior art patents.

Illustrative of one class of polymers, the polyurethane is suitably irradiated to convert the thermoplastic polyurethane to a thermoset polyurethane is suitably effected using a beam of photons, preferably from a source of high energy ionizing photons, in order to cause cross-linking of the thermoplastic polyurethane composition to occur. The radiation source suitably provides the desired irradiation of the thermoplastic polyurethane. As used herein, the term "irradiation", in the context of the photon beam employed in the present invention, is used expansively to encompass bombardment of the target thermoplastic polyurethane with photons, e.g. beta (also referred to herein as e-beam) particles, gamma particles, ultraviolet ("uv") radiation, combinations thereof, and the like, in order to effect conversion of the TPU to the desired thermoset polyurethane. Although the energy output from the radiation source to the thermoplastic polyurethane composition can vary over a wide range, it is preferred that, when using e-beam irradiation, an amount of radiation of from about 1 and about 100 Mega Rads, more preferably between 10 and 50 Mega Rads, most preferably between 10 and 20 Mega Rads, be imparted to the composition over a suitable period of time to insure that the polyurethane being irradiated does not overheat.

As used herein, the term "thermoplastic" is used in its broad sense to designate a material that is reprocessable at an elevated temperature, whereas "thermoset" designates a material that exhibits high temperature stability without such reprocessability at elevated temperatures. The term "thermoplastic elastomer" designates a material that possesses an elastic, rubber-like property such that it exhibits at least a one hundred percent elongation without breaking when stretched at room temperature, and will return to its unstretched length when released. Useful thermoplastics include extrudable solid polymers, powder coating polymers, as well as sprayable polymers.

As used herein, the term "allylic monomer" is intended to designate a cross-linking moiety for polyurethanes that is monomeric and contains an allyl group. Preferably, the allylic monomer is free of peroxide, acrylate, and methacrylate moieties.

Particularly useful reactive monomers include, for example, triallylisocyanurate (also referred to herein as "TAC"), triallylcyanurate (also referred to herein as "TAC"), diallyl phthalate (also referred to herein as "DAP"), and meta-phenylene dimaleimide (also referred to herein as MPDM), and combinations thereof. The TAIC is commercially available as a liquid dispersion, and, alternatively, on a silicate substrate (75% TAIC on 25% silicate) as SYNPRO PLC-4185, a product of the Synthetic products Co. Although less desired, other useful reactive monomers include methacrylate-containing monomers, such as trimethylolopropane trimethacrylate (TMPTMA), commercially available as Sartomer's SR-350.

When the selected polymer is a polyurethane, the reactive monomer is suitably admixed with the polyurethane-forming composition prior to preparation of the TPU, or admixed with the TPU prior to preparation of the desired thermoset polyurethane product.

Although not wishing to be bound by any particular theory, it is believed that the essentially discoloration-free appearance of the thermoset polyurethanes produced in accordance with the present invention is attributable to the use of an aliphatic polyisocyanate in the polyurethane-forming compositions employed in the present invention. The present inventor has found that the irradiation employed in the present invention does not significantly discolor the aliphatic polyisocyanate-based polyurethane compositions employed in this invention. In contrast, such irradiation appears to severely discolor comparison polyurethane compositions based upon aromatic polyisocyanates. Further, the present inventor has found that aliphatic polyisocyanate-based TPUs are suitably converted to thermoset composition in the presence of allylic monomers by irradiation, whereas the benzene molecules in the backbone of aromatic polyisocyanate-based TPU's seem to absorb high energy radiation (e-beam or gamma rays), thus rendering aromatic isocyanate-based TPU's stable (and, hence, not easily thermoset) in the presence of irradiation. Moreover, although aromatic polyisocyanate-based TPU's typically exhibit better chemical properties, such as resistance to organic solvents and oils, than prior art aliphatic polyisocyanate-based TPU, the compositions of the present invention overcome this disadvantage since the thermoset polyurethanes of the present invention exhibit excellent physical and chemical properties.

The aliphatic polyisocyanate useful as a reactant in forming the polyurethanes employed in the present invention is preferably selected from commercially-available aliphatic polyisocyanates such as, for example, 1,6-hexamethylene diisocyanate ("HDI"), isophorone diisocyanate ("IPDI"), ethylene diisocyanate, 1,4-tetramethylene diisocyanate, 2,2, 4-trimethyl-1,6-hexamethylene diisocyanate, 1,10-decanemethylene diisocyanate, 1,12-dodecanemethylene diisocyanate, cyclohexane-1,3-diisocyanate, cyclohexane-1, 4-diisocyanate, 1-isocyanato-2-isocyanatomethyl cyclopentane, isophorone diisocyanate, bis-(4-isocyanatocyclohexyl)-methane, 1,3- and/or 1,4-bis-(isocyanatomethyl)-cyclohexane, bis- (4-isocyanato-3-methyl-cyclohexyl)-methane, 1-isocyanato-1-methyl-4(3)-isocyanatomethyl cyclohexane, 4,4'-dicyclohexylmethane diisocyanate, and combinations thereof.

The "polyahl" useful as a reactant in forming the polyurethanes employed in the present invention is an active hydrogen-containing compound that is reactive with the aliphatic polyisocyanate to produce the desired polyurethane. In addition, the term polyahl is intended to encompass compounds that react to generate an active hydrogen-containing moiety such as imines. An active hydrogen group is a group which has a hydrogen atom which, because of its position in the molecule, displays activity according to the Zerewitnoff test described by Woller in the Journal of American Chemical Society, Vol. 49, page 3181 (1927). Illustrative of such active hydrogen groups are —OH, —NH—, —COOH, —SH and —CONH—. Particularly suitably polyahls include polyols, imines (such as ketimines and aldimines), oxazolidines, and combinations thereof, preferably having a weight average molecular weight of between about 100 and about 10,000, more preferably between about 100 and about 5,000, most preferably between about 200 and about 2,000.

Suitable amines are aliphatic or cycloaliphatic, primary or secondary amines. Preferred amines are poly(alkyleneoxy) alkylamines.

Suitable polyols include polyether polyols and polyester polyols. The preferred polyols useful in the present invention have a hydroxyl functionality of no greater than about 2, more preferably less than 1.5, advantageously about 1, in order to prevent the formation of very high molecular weight polyurethane prepolymers which result in coating viscosities higher than desired for ready application. The polyether polyols are prepared by polymerization of alkylene oxides with water, polyhydric alcohols with two to eight hydroxyl groups, or amines. Polyester polyols are suitably prepared by a condensation reaction of a polycarboxylic acid with a polyhydric alcohol. Another useful polyol is polybutadiene glycol ("PBDG").

In preparing the polyurethanes useful in the present invention, the ratio of NCO equivalents in the polyisocyanate to the OH equivalents in the active hydrogen-containing compound can vary over a wide range of between about 10:1 and about 1:10, preferably between about 2:1 and about 1:2.

Catalysts are typically employed in the polyurethane-forming reaction. Useful catalysts include those which facilitate the reaction of the polyahl with the aliphatic polyisocyanate reactants. Suitable catalysts are the organotin catalysts, alone or in combination with amine catalysts, particularly tertiary amine catalysts. Illustrative organotin catalysts include dibutyltin dilaurate, stannous octoate, and combinations thereof. Illustrative amine catalysts include the following: N,N'-dimethylethanolamine, N,N-dimethylamino-ethoxyethanol, N,N'-dimethylaminoethyl-N-methylethanolamine, N,N-dimethyl-N',N'-2-hydroxypropyl-1,3-propylene diamine, N,N,N'-trimethyl-N'-hydroxyethyl-bis(amino ethyl)ether, N,N-bis(3-dimethylaminopropyl)amino-2-propanol, and combinations thereof. The catalysts are suitably employed in the polyurethane-forming formulation in a total amount of between about 0.01% and about 5%, preferably between about 0.01% and about 1%, by weight based upon the weight of the polyurethane-forming composition.

In preparing the desired polyurethane, the polyether polyol(s), polyisocyanate(s), chain extender(s) such as polyether or polyester glycol chain extenders, and other desired components are reacted, typically at an elevated temperature. One method of forming the desired thermoplastic polyurethane is by continuous processing utilizing an extruder, as illustrated by the disclosures of U.S. Pat. No. 3,642,964, incorporated herein by reference in its entirety. An alternative method involves batch processing, followed by grinding and extrusion of the formed elastomer as is well-known in the art. Although either the prepolymer method or the one-shot method can be used, the one-shot method is preferred. The one-shot method is intended to also include the process whereby the diisocyanate has been converted to a quasi-prepolymer by reaction with a minor amount (i.e., less than about 10 percent on an equivalent basis) of polyol prior to carrying out the polyurethane forming reaction.

In preparing the desired polyurethane, urethane forming catalysts can be used, as discussed above, as well as the usual compounding ingredients such as antioxidants or other antidegradants. Typical antioxidants include hindered phenols, butylated hydroxytoluene ("BHT"), and the like. Other optional compounding ingredients include, for example, plasticizers, adhesion promoters, fillers and pigments like clay, silica, fumed silica, carbon black, talc, phthalocyanine blue or green, $TiO_2$, U-V absorbers, $MgCO_3$, $CaCO_3$ and the like. The compounding ingredients are suitably employed in an amount of between 0 and about 75 weight percent based upon the weight of the elastomer. The polymerization reaction may be carried out in a single reaction (one-shot process), or in one or more sequential steps (prepolymer process), using either bulk polymerization or solution polymerization. When solution polymerization is used, polar solvents such as tetrahydrofuran ("THF"), dimethylformamide ("DMF"), and dimethylacetamide ("DMAC") are typically utilized. In the one-shot process, all the isocyanate-reactive components are reacted simultaneously with the polyisocyanate. In such process, it is normal practice to blend all components except the polyisocyanate into a "B-side" mixture, which is then reacted with the polyisocyanate to form the polyurethane and/or polyurea elastomer. However, the order of mixing is not critical as long as the components do not undesirably react before all components are present. The reaction mixture is then suitably placed in a mold, or extruded through an extruder, and cured at a suitable temperature. The apparatus used for blending and molding is not especially critical. Hand mixing, conventional machine mixing, and the so-called reaction injection molding (RIM) equipment are all suitable. In the prepolymer process, all or a portion of one or more of the isocyanate reactive materials is reacted with a stoichiometric excess of the polyisocyanate to form an isocyanate-terminated prepolymer. This prepolymer is then allowed to react with the remaining isocyanate-reactive materials to prepare the polyurethane and/or polyurea elastomer. The prepolymer can be prepared with either the polyether or the chain extender, or a mixture of both.

The mixing of the reactants can be carried out at ambient temperature (typically from 20NC to 25NC) and the resulting mixture is then heated to a temperature of the order of about 40NC to about 130NC, preferably to a temperature of about 90NC to about 120NC. Alternatively, and preferably, one or more of the reactants is preheated to a temperature within the above ranges before the admixing is carried out. Advantageously, in a batch procedure, the heated reaction components are subjected to degassing in order to remove entrained bubbles of air, water, or other gases before the reaction takes place. This degassing is accomplished conveniently by reducing the pressure under which the components are maintained until no further evolution of bubbles occurs. The degassed reaction components are then admixed and transferred to suitable molds or extrusion equipment or the like and cured at a temperature of the order of about 20NC to about 115NC. The time required for curing will vary the temperature of curing and also with the nature of the particular composition, as is known in the art.

The polymers produced in accordance with the present invention are useful in a variety of applications, including sealants, elastomers, coatings, adhesives, and in the fabrication of a wide variety of household, commercial, and industrial products. For example, the present invention is suitably employed to produce crosslinked polymers that are useful in producing medical catheters, angioplasty balloons, and male and female birth control sheath products. The crosslinked polymer product retains its flexural modulus at body temperatures longer than catheters made from prior art TPU's. As another illustration, the present invention is suitably employed to produce flexible wire and cable jackets having improved temperature and fluid resistance, as compared analogous products made from prior art TPU's. Other illustrative uses for the thermoset polymers produced in accordance with the present invention include the following: orthodontic ligatures which last longer than those made from prior art TPU's; seals, gaskets and o-rings which are easier to fabricate than those made from prior art cast polyurethanes and exhibiting better temperature stability, compression set and fluid resistance than those made from prior art TPU's; sneaker and shoe soles that are longer wearing than those made from prior art TPU's; longer lasting toner wiper blades for copiers and laser printers, as compared to those made from prior art TPU's; and, medical implanted devices and coated wires which last longer inside body parts and cavities than those made from prior art TPU's. Heat shrinkable film and heat shrinkable tubing may also be made from the composition of the invention.

The polymer employed in the present invention is suitably shaped into the desired product configuration while in the thermoplastic state, and then irradiated to thermoset the polyurethane product. The thermoplastic polymer can be in solid form, such as pellets, prior to heating and forming the desired polymer product. Alternatively, solid thermoplastic polymer can be dissolved in organic solvent, and used for dipping, spraying or otherwise coating the dissolved polymer onto a substrate, and then the coating is suitably thermoset by irradiation.

As used herein, the term "molecular weight" is intended to designate number average molecular weight. All percents used herein are percents by weight unless otherwise specified. As used herein, the term "phr" denotes "parts by weight per hundred parts of resin".

The following Example is intended to illustrate, but in no way limit the scope of, the present invention.

EXAMPLE 1

Part A—Preparation and Testing of a Thermoset Polyurethane of the Present Invention A sample of dried aliphatic polyester, thermoplastic polyurethane resin, having a hardness of 80 Shore A and a melt index of 2 at 165EC, was compounded with 4 phr of SYNPRO PLC-4185 (75% TAIC on 25% silicate) allylic monomer to yield a mixture containing 3 phr TAIC. This mixture was compression molded at 125EC for 10 minutes to yield a 6"×6"×0.070" plaque. The plaque was exposed to 14 Mega Rads of high energy electron beam irradiation in order to convert the plaque to a thermoset plaque.

After irradiation the thermoset plaque was tested for various physical properties in accordance with ASTM tests as identified in Table 1 below. The test results are provided in Table 1.

TABLE 1

| Physical Properties | 14 MRads |
| --- | --- |
| Ultimate elongation at break (%) | 425 |
| 200% Modulus (psi) | 900 |
| Compression set (%) | 58.5 (72 hours at 100EC) |
| Color change (visual) | minimal |

| Fluid Resistance | | | 14 MRads |
| --- | --- | --- | --- |
| Fluid | Temp | Time | Observation |
| Mil-L-16884 | 121EC | 2.5 hrs | swell + 13%, brown stained, somewhat tacky |
| Tetrahydrofuran | 20EC | 2.5 hrs | swelled, very friable, did not dissolve** |
| 100% IPA* | 20EC | 2.5 hrs | no change |
| 50% IPA* | 20EC | 2.5 hrs | no change |
| Water, distilled | 20EC | 2.5 hrs | no change |

(*IPA = isopropyl alcohol)
(**unirradiated pellets completely dissolved)

Part B—Temperature Stability Test

The irradiated polyurethane of Part A above did not melt or flow at elevated temperatures as demonstrated by probing the irradiated plaque with an electrically heated solder iron tip at a temperature of approximately 300EC.

Part C—Comparison With Aromatic Polyisocyanate-based Polyurethanes

Dow's PELLETHANE 55D aromatic polyisocyanate-based polyurethane resin was compounded with 3 phr TAIC allylic monomer, and exposed to 15 Mrads of high energy electron beam irradiation. No crosslinking was observed based upon the results of a hot iron test (described hereinabove) on this composition, and the physical properties were unchanged relative to the unirradiated neat pellets. Instead, the irradiated material discolored by turning dark brown.

In a second experiment, Dow's PELLETHANE 55D aromatic polyisocyanate-based polyurethane resin Pellethane 55D was compounded with 3 phr of TMPTMA (an acrylic monomer) and exposed to 15 Mrads of high energy electron beam irradiation. No crosslinking was observed in the hot iron test as described above, and the physical properties were unchanged relative to the unirradiated neat pellets. The irradiated material turned dark brown.

Part D—Comparison of Crosslinked Versus Uncrosslinked TPUs in a Weighted Probe Test A comparison was made between the physical property stability of a crosslinked polymer and that of an uncrosslinked polymer when exposed to elevated temperatures using a Thermo-Mechanical Analyzer ("TMA"). Briefly, the test regimen was conducted by placing a small piece (approximately 2 millimeters thick) of polymer is heated to an elevated temperature in the TMA, and a round glass probe weighted to 5 grams is applied to the sample. The sample was heated in the TMA to provide a controlled rate of temperature increase of 5 degrees Centigrade per minute, and the resulting probe penetration into the sample of TPU was recorded as a function of time. The test results showed that the probe caused heat deformation of the uncrosslinked TPU at a much lower temperature than that at which it caused deformation of the crosslinked TPU. By way of illustration, uncrosslinked TPU was initially penetrated by the probe at a polymer temperature of 115 degrees Centigrade. In contrast, TPU exposed to 20 MRads of radiation before being placed in the TMA resisted initial penetration until a polymer temperature of 239 degrees Centigrade was reached. These results demonstrate the improved dimensional heat stability of the crosslinked TPU as compared to the uncrosslinked TPU.

EXAMPLE 2

Physical Property Testing of Block Copolymers Before and After Irradiation

Samples of several block copolymers were prepared and tested as follows: Each polymer identified in Table 2 below was mixed with 3% (by weight) of pure liquid TAIC (triallyisocyanurate) in a twin screw extruder, and the resulting mixture was strand extruded and pelletized. The extruded product was dryed and compression molded into plaques having dimensions of 6 inches×6 inches×0.080 inches, and then irradiated with electron beam irradiation at the indicated dosage shown in Table 1 below.

Tensile bars of the extruded product were die cut and the tensile strength and elongation at break for these samples were measured. The melting ability of these samples was determined by applying a hot instrument to them. The results are displayed in Table 1 below.

TABLE 2

| Change in physical properties related to radiation dose for certain modified polymers | | | | | |
| --- | --- | --- | --- | --- | --- |
| Material | Dose* | Color | Melts | Tb** | Eb*** |
| Pebax-72D | 0 | white | yes | 6460 | 190 |
| " | 10 | green | no | 6740 | 105 |
| " | 12.5 | green | no | 6770 | 95 |
| " | 15 | green | no | 6800 | 90 |
| Hytril-72D | 0 | white | yes | 4895 | 200 |
| " | 10 | white | no | 4890 | 170 |
| " | 12.5 | white | no | 4180 | 20 |
| " | 15 | grey | no | 4830 | 15 |

(*Units are in MegaRads).
(**Tensile strength at break in psi).
(***Elongation at break in percent).

The results as provided in Table 2 above demonstrate that Hytril and PEBAX block co-polymers having a Shore D hardness of 72, exhibit changes in mechanical properties consistent with crosslinking of these polymers. The HYTRIL polymer is a co-polyester polymer of poly(1,4 butanediol terephthalate) and poly(alkylene ether terephthalate), whereas the PEBAX polymer is a co-poly (ether-ester-amide) polymer. Both polymers exhibit decreasing elongation with increasing radiation dose, and both no longer melt at the temperature tested, namely 325 degrees Centigrade, at high radiation doses. In addition, PEBAX polymer shows an increase in tensile strength with increased radiation dose, while the tensile strength of HYTRIL polymer is essentially unchanged with increased radiation dose.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A radiation cross-linkable composition, comprising:
    (a) a thermoplastic copolymer selected from the group consisting of a copolyester copolymer of poly(1,4-butanediol terephthalate) and poly(alkylene ether terephthalate), and copolymers of polylaurinlactam and polytetrahydrofuran, and
    (b) a monomer cross-linker selected from the group consisting of allylic monomers, acrylate monomers, methacrylate monomers, meta-phenylene dimaleimide, and combinations thereof for conversion of at least a portion of said thermoplastic copolymer from a thermoplastic to a thermoset state upon irradiation of said composition with energy from a radiation, source.

2. The radiation-crosslinkable composition of claim 1 wherein said energy is in the form of free radical initiating or ionizing radiation selected from the group consisting of photons, beta-particles and gamma-particles, ultraviolet radiation, electron beam radiation, and combinations thereof.

3. The radiation-crosslinkable composition of claim 1, wherein said thermoplastic copolymer is a block copolymer containing hard and soft segment.

4. The radiation-crosslinkable composition of claim 1, wherein said thermoplastic copolymer is a thermoplastic elastomer.

5. The radiation-cross-linkable composition of claim 1, wherein said monomer cross-linker is selected from the group consisting of triallylisocyanurate, triallylcyanurate, diallyl phthalate, trimethylolpropane trimethacrylate, and combinations thereof.

6. A radiation cross-linked composition made by irradiating the radiation crosslinkable composition of claim 1 with energy from a radiation source.

7. The radiation crosslinked composition of claim 6, wherein said radiatin crosslinked composition is in the form of a device selected from the group consisting of surgical gloves, angioplasty balloons, birth control sheathes, heat shrinkable tubing, heat-shrinkable film, wire and cable jackets, orthodontic ligatures, seals, gaskets, o-rings, shoe soles, toner wiper blades, medical implant devices, and coated wires.

8. A radiation cross-linkable composition, comprising:
    (a) thermoplastic copoly(ether-ester-amide) polymer and
    (b) a monomer cross-linker selected from the group consisting of allylic monomers, acrylate monomers, methacrylate monomers, meta-phenylene dimaleimide, and combinations thereof for conversion of at least a portion of said thermoplastic copolymer from a thermoplastic to a thermoset state upon irradiation of said composition with energy from a radiation source, with the proviso that the allylic monomer is other than triallylisocyanurate ("TAIC") or triallylcyanurate ("TAC").

9. The radiation-crosslinkable composition of claim 8 wherein said energy is in the form of free radical initiating or ionizing radiation selected from the group consisting of photons, beta-particles and gamma-particles, ultraviolet radiation, electron beam radiation, and combinations thereof.

10. The radiation-crosslinkable composition of claim 8, wherein said thermoplastic copolymer comprises a block copolymer containing hard and soft segments.

11. The radiation-crosslinkable composition of claim 8, wherein said thermoplastic copolymer comprises a thermoplastic elastomer.

12. A radiation cross-linked composition made by irradiating the radiation crosslinkable composition of claim 8 with energy from a radiation source.

13. The radiation crosslinked composition of claim 12, wherein said radiation crosslinked composition is in the form of a device selected from the group consisting of surgical gloves, angioplasty balloons, birth control sheathes, heat shrinkable tubing, heat-shrinkable film, wire and cable jackets, orthodontic ligatures, seals, gaskets, o-rings, shoe soles, toner wiper blades, medical implant devices, and coated wires.

14. A radiation cross-linkable medical catheter made from a thermoplastic cross-linkable composition, said thermoplastic cross-linkable composition comprising:
    (a) a thermoplastic polymer selected from the group consisting of a copolyester copolymer of poly(1,4-butanediol terephthalate) and poly(alkylene ether terephthalate), copolymers of polylaurinlactam and polytetrahydrofuran, and a reaction product of an aliphatic polyisocyanate and a polyahl; and
    (b) a monomer cross-linker selected from the group consisting of allylic monomer crosslinkers, methacrylate monomer crosslinkers, meta-phenylene dimaleimide, and combinations thereof; said monomer cross-linker present in said composition in an amount sufficient to provide cross-linking of at least a potion of said thermoplastic polymer from a thermoplastic to a thermoset state upon irradiation of said composition with energy from a radiation source.

15. The radiation cross-linkable medical catheter of claim 14, wherein said thermoplastic polymer is a thermoplastic elastomer.

16. The radiation cross-linkable medical catheter of claim 14, wherein said thermoplastic polymer is a block copolymer containing hard and soft segments.

17. The radiation cross-linkable medical catheter of claim 14, wherein said monomer cross-linker is selected from the group consisting of triallylisocyanurate, triallylcyanurate, diallyl phthalate, metaphenylenedimaleimide, trimethylolpropane trimethacrylate, and combinations thereof.

18. A radiation cross-linked medical catheter made by irradiating the radiation crosslinkable medical catheter of claim 14 with energy from a radiation source.

19. The radiation crosslinked medical catheter of claim 18, wherein said energy is in the form of free radical initiating or ionizing radiation selected front the group consisting of beta particles, gamma particles, ultraviolet radiation, electron beam radiation, and combinations thereof.

20. A radiation cross-linkable medical catheter made from a thermoplastic cross-linkable composition, said thermoplastic cross-linkable composition comprising:
    (a) a thermoplastic polymer selected from the group consisting of nylon, and a copoly(ether-ester-amide) polymer; and
    (b) a monomer cross-linker selected from the group consisting of allylic monomer crosslinkers, methacrylate monomer crosslinkers, meta-phenylene dimaleimide, and combinations thereof; said monomer cross-linker present in said composition in an amount sufficient to provide cross-linking of at least a portion of said thermoplastic polymer from a thermoplastic to a thermoset state upon irradiation of said composition with energy from a radiator source, with the proviso that the allylic monomer is other than triallylisocyanurate ("TAIC") or triallylcyanurate ("TAC").

21. The radiation cross-linkable medical catheter of claim 20, wherein said thermoplastic polymer is a thermoplastic elastomer.

22. The radiation cross-linkable medical catheter of claim 20, wherein said thermoplastic polymer is a block copolymer containing hard and soft segments.

23. The radiation cross-linkable medical catheter of claim 20, wherein said monomer cross-linker is selected from the group consisting of diallyl phthalate, metaphenylenedimaleimide, trimethylolpropane trimethacrylate, and combinations thereof.

24. A radiation cross-linked medical catheter made by irradiating the radiation crosslinkable medical catheter of claim 20 with energy from a radiation source.

25. The radiation crosslinked medical catheter of claim 24, wherein said energy is in the form of free radical initiating or ionizing radiation selected from the group consisting of beta particles, gamma particles, ultraviolet radiation, electron beam radiation, an combinations thereof.

26. A radiation cross-linkable medical angioplasty balloon made from a thermoplastic cross-linkable composition, said thermoplastic cross-linkable composition comprising:

(a) a thermoplastic polymer selected from the group consisting of nylon, a copolyester copolymer of poly (1,4-butanediol terephthalate) and poly(alkylene ether terephthalate), a copoly(ether-ester-amide) polymer, and copolymers of polylaurinlactam and polytetrahydrofuran, and a reaction product of an aliphatic polyisocyanate and a polyahl; and (b) a monomer cross-linker selected from the group consisting of allylic monomer crosslinkers, methacrylate monomer crosslinkers, meta-phenylene dimaleimide, and combinations thereof; said monomer cross-linker present in said composition in an amount sufficient to provide cross-linking of at least a portion of said thermoplastic polymer to convert said portion from a thermoplastic to a thermoset state upon irradiation of said composition with energy from a radiation source.

27. The radiation cross-linkable medical angioplasty balloon of claim 26, wherein said thermoplastic polymer is a thermoplastic elastomer.

28. The radiation cross-linkable medical angioplasty balloon of claim 26, wherein said thermoplastic polymer is a block copolymer containing hard and soft segments.

29. The radiation cross-linkable medical angioplasty balloon of claim 26, wherein said monomer cross-linker is selected from the group consisting of triallylisocyanurate, triallylcyanurate, diallyl phthalate, metaphenylenedimaleimide, trimethylolpropane trimethacrylate, and combinations thereof.

30. A radiation cross-linked medical angioplasty balloon made by irradiating the radiation crosslinkable medical angioplasty balloon of claim 26 with energy from a radiation source.

31. The radiation crosslinked medical angioplasty balloon of claim 30, wherein said energy is in the form of free radical initiating or ionizing radiation selected from the group consisting of beta particles, gamma particles, ultraviolet radiation, electron beam radiation, and combinations thereof.

32. A radiation cross-linked medical angioplasty balloon made from a cross-linked composition, wherein said cross-linked composition is produced by irradiating a crosslinkable composition comprising:

(a) a thermoplastic polymer selected from the group consisting of nylon, a copolyester copolymer of poly (1,4-butanediol terephthalate) and poly(alkylene ether terephthalate), a copoly(ether-ester-amide) polymer, and copolymers of polylaurinlactam and polytetrahydrofuran, and a reaction product of an aliphlatic polyisocyanate and a polyahl; and (b) a monomer cross-linker selected from the group consisting of allylic monomer crosslinkers, methacrylate monomer crosslinkers, meta-phenylene dimaleimide, and combinations thereof; said monomer cross-linker present in said composition in an amount sufficient to cross-link at least a portion of said thermoplastic polymer to convert said portion from a thermoplastic to a thermoset state upon irradiation of said composition with energy from a radiation source.

33. The radiation cross-linked medical angioplasty balloon of claim 32, wherein said thermoplastic polymer is a thermoplastic elastomer.

34. The radiation cross-linked medical angioplasty balloon of claim 32, wherein said thermoplastic polymer is a block copolymer containing hard and soft segments.

35. The radiation crosslinked medical angioplasty balloon of claim 32, which is produced by irradiating said crosslinkable composition with energy in the form of free radical initiating or ionizing radiation selected from the group consisting of beta particles, gamma particles, ultraviolet radiation, electron beam radiation, and combinations thereof.

36. The radiation cross-linked medical angioplasty balloon of claim 32, wherein said monomer cross-linker is selected from the group consisting of triallylisocyanurate, triallylcyanurate, diallyl phthalate, metaphenylenedimaleimide, trimethylolpropane trimethacrylate, and combinations thereof.

* * * * *